United States Patent
Lawrence et al.

(10) Patent No.: US 6,890,765 B2
(45) Date of Patent: May 10, 2005

(54) PARTICLES FOR IMMUNOASSAYS AND METHODS FOR TREATING THE SAME

(75) Inventors: Christopher C. Lawrence, Fishers, IN (US); Wei Yuan, Fishers, IN (US); Armen B. Shanafelt, Carmel, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 292 days.

(21) Appl. No.: 10/025,196

(22) Filed: Dec. 18, 2001

(65) Prior Publication Data

US 2003/0087458 A1 May 8, 2003

Related U.S. Application Data

(63) Continuation-in-part of application No. 10/053,058, filed on Nov. 2, 2001, now abandoned.

(51) Int. Cl.[7] .................. G01N 33/546; G01N 33/547; G01N 33/551; G01N 33/553
(52) U.S. Cl. ................. 436/533; 436/524; 436/525; 436/527; 436/825; 436/826; 436/909
(58) Field of Search ................. 436/525, 527, 436/524, 533, 825, 826, 909

(56) References Cited

U.S. PATENT DOCUMENTS

| | | | |
|---|---|---|---|
| 4,292,038 | A | 9/1981 | Kondo et al. |
| 4,362,531 | A | 12/1982 | de Steenwinkel et al. |
| 4,536,478 | A | 8/1985 | Sokoloff et al. |
| 5,486,479 | A | 1/1996 | Ito et al. |
| 5,506,151 | A | 4/1996 | Ito et al. |
| 5,643,732 | A | 7/1997 | Strahilevitz |
| 5,846,751 | A | 12/1998 | Pronovost et al. |
| 6,030,845 | A | 2/2000 | Yamao et al. |
| 6,203,706 | B1 | 3/2001 | Schwind et al. |
| 6,274,325 | B1 | 8/2001 | Deger et al. |

FOREIGN PATENT DOCUMENTS

| | | | |
|---|---|---|---|
| EP | 0 679 892 A1 | | 11/1995 |
| WO | WO 97/06166 | * | 2/1997 |
| WO | WO 98/36277 | * | 8/1998 |
| WO | WO 02/03068 A1 | | 1/2002 |

OTHER PUBLICATIONS

M. Dijksma et al, Anal. Chem. 73(5), 901–907 (Jan. 27, 2001).*
T.J. Inzana, J. Clin. Microbiol., 33, 2297–2303 (1995).*
European Search Report from corresponding European Application No. 02 02 4080, dated May 7, 2003, 4 pages.*
J.L. Ortega–Vinuesa et al. *J. Biomater. Sci. Polymer Edn.*, 12(4), 379–408 (2001).
C.R. Martin et al. *Analytical Chemistry—News & Features*, May 1, 1998, 322A–327A.
R.G. Chapman et al. *J. Am. Chem. Soc.*, 122, 8303–8304 (2000).
N. Nakajima and Y. Ikada, *Bioconjugate Chem.*, 6, 123–130, (1995).
M. Yamaguchi et al. *J. Health Science*, 47(4), 419–423 (2001).
S. Perez–Amodio et al. *Anal. Chem.*, 73, 3417–3425 (2001).
P. Holownia et al. *Anal. Chem.*, 73, 3426–3431 (2001).
A. Singh et al. *J. Biosci.*, 25(1), 47–54 (2000).
J. Sackrison, "Covalent Coupling And Diagnostic Development Using Microspheres", 17 pages (1996).
Bangs Laboratories, Inc., Tech Note #13c—"Covalent Coupling Protocols", 9 pages.

* cited by examiner

*Primary Examiner*—Mary E. Ceperley
(74) *Attorney, Agent, or Firm*—Marilyn L. Amick; Roche Diagnostics Operations, Inc.

(57) ABSTRACT

A method of treating particles to be used in immunoassays reduces interference in particle agglutination assays. For particles having covalently bound antibodies and residual NHS-ester or sNHS-ester groups on the surface, the reactive esters are treated with an aqueous mixture containing an amine compound of formula (I):

$$H_2N-R-X \qquad (I).$$

The moiety —X is —$NH_2$, —OH, or —$CO_2CH_2CH_3$; and R is an alkyl group or an alkyl ether group. When —X is —$NH_2$ or —$CO_2CH_2CH_3$, R contains from 1 to 20 carbon atoms; and when —X is —OH, R contains from 4 to 20 carbon atoms.

14 Claims, 3 Drawing Sheets

12.5 mM TEO

No TEO present

PARTICLES FOR IMMUNOASSAYS AND METHODS FOR TREATING THE SAME

This application is a continuation-in-part of U.S. patent application Ser. No. 10/053,058, filed Nov. 2, 2001 now abandoned entitled "Particles For Immunoassays And Methods For Treating The Same" filed Nov. 2, 2001, with inventors C. C. Lawrence et al., which is incorporated herein by reference.

BACKGROUND OF THE INVENTION

In testing for analytes such as drug molecules, immunoassays have proven to be especially useful. In an immunoassay, the interaction of an analyte, sometimes referred to as an antigen, with a specific receptor, typically an antibody, results in the formation of an antigen-antibody complex. This complex can be detected by various measurements, such as radioactivity, fluorescence, light absorption and light scattering. The results are then correlated with the presence, absence, and ideally the concentration of the analyte.

One type of particle-based agglutination immunoassay is based on the binding of an antigen with a particle-bound antibody. The particles employed are generally polymer particles, such as polystyrene and poly(methyl methacrylate), and are typically produced by an emulsion polymerization process. Other particle systems may also be used, including gold particles such as gold nanoparticles and gold colloids; and ceramic particles, such as silica, glass, and metal oxide particles. The antibody may be physically adsorbed onto the particle; however, greater stability and longer shelf-life are obtained when the antibody is covalently attached. See for example J. L. Ortega-Vinuesa et al. *J. Biomater. Sci. Polymer Edn.*, 12(4), 379–408 (2001).

Particles having covalently bound antibodies are typically prepared by activation of the particles, followed by coupling of antibodies to the activated particles. For particles having carboxylate groups bound to the surface, activation is often achieved by contacting the particles with a solution of a carbodiimide coupling reagent and a succinimide reagent such as N-hydroxysuccinimide (NHS) or N-hydroxysulfosuccinimide (sNHS). The carboxylate groups on the surface are thus converted into NHS-ester or sNHS-ester groups. Carbodiimide couplers include, for example, N-ethyl-N'-(3-dimethyl-aminopropyl) carbodiimide (EDC); dicyclohexylcarbodiimide (DCC); and diisopropylcarbodiimide (DIC). Antibodies, for example IgG, can then be coupled to the particles by mixing the activated particles and the antibodies in an aqueous mixture, thereby forming sensitized particles. An illustration of this process is given in the following reaction scheme.

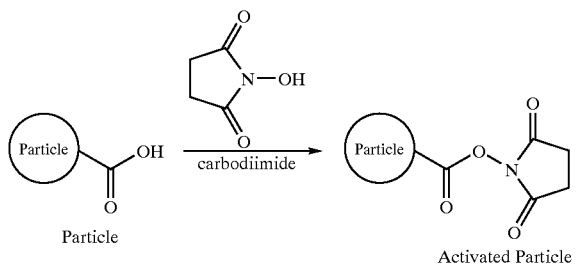

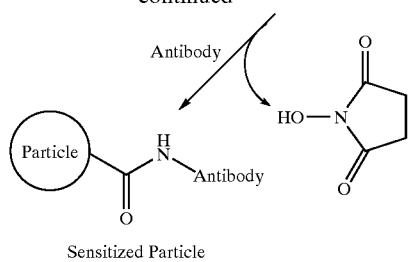

Sensitized Particle

The sensitized particles typically are then treated with a post-blocker, for example bovine serum albumin (BSA). In these processes covalent linkages, for example amide linkages (—NH—C(=O)—), are formed between the particle surface and the antibody and between the particle surface and the BSA. These covalent linkage formations are not typically exhaustive, and residual NHS-esters or sNHS-esters can remain on the particle surface.

When sensitized particles are mixed in an aqueous environment with a sample to be analyzed, the antigen in the sample will specifically bind to the antibody, thus causing the particles to agglutinate into clusters of particles having a larger collective size than that of an individual particle. This agglutination can be detected by measuring the change in the absorbance or the scattering of light by the sample. Ideally, the degree of agglutination in a particle-based agglutination immunoassay can be correlated with the amount of antigen in the sample. However, non-specific interactions between the particles and the sample can result in agglutination of the particles which is unrelated to the antigen-antibody interaction. These unwanted interactions can cause false positive or false negative results, and can also lead to inaccurate correlations of the agglutination response to the concentration of the antigen of interest.

It is believed that residual NHS-esters or sNHS-esters on particle surfaces can undergo non-specific chemical reactions with sample components, with polypeptide sample components being especially problematic. In order to minimize non-specific binding, sensitized particles have conventionally been treated with an amine compound such as glycine or ethanolamine to react with these esters before the particles are used in immunoassays (U.S. Pat. No. 5,486,479). These efforts have met with mixed success.

It is thus desirable to prevent chemical reactions between particle-bound NHS-esters or sNHS-esters and sample components. It is also desirable to provide a modified particle surface which inhibits adsorption of sample components onto the surface.

SUMMARY OF THE INVENTION

In one aspect of the invention, there is a method of preparing particles for immunoassays, comprising reacting particles comprising carboxylate groups with N-hydroxysuccinimide or N-hydroxysulfosuccinimide and with a carbodiimide coupling reagent to provide activated particles comprising succinimide ester groups; contacting said activated particles with antibodies to provide sensitized particles comprising covalently bound antibodies and residual succinimide esters; and treating said sensitized particles in an aqueous mixture with an amine compound of formula (I):

$$H_2N—R—X \qquad (I);$$

wherein —X is selected from the group consisting of —$NH_2$, —OH, and —$CO_2CH_2CH_3$; and R is selected from the group consisting of an alkyl group and an alkyl ether group; wherein, when —X is —NH$_2$ or —CO$_2$CH$_2$CH$_3$, R comprises from 1 to 20 carbon atoms; and when —X is —OH, R comprises from 4 to 20 carbon atoms.

In another aspect of the invention, there is a sensitized particle for use in immunoassays, comprising: a particle comprising a surface; at least one antibody bound to the surface through a covalent bond; and the reaction product of a succinimide ester and an amine compound of formula (I) on the surface;

H$_2$N—R—X  (I);

wherein —X is selected from the group consisting of —NH$_2$, —OH, and —CO$_2$CH$_2$CH$_3$; and R is selected from the group consisting of an alkyl group and an alkyl ether group; wherein, when —X is —NH$_2$ or —CO$_2$CH$_2$CH$_3$, R comprises from 1 to 20 carbon atoms; and when —X is —OH, R comprises from 4 to 20 carbon atoms.

In yet another aspect of the invention, there is a particle for use in immunoassays, comprising: a polymer particle comprising a surface; at least one antibody bound to the surface through a covalent bond; BSA on the surface; and the reaction product of a succinimide ester and an amine compound on the surface; wherein the amine compound is selected from the group consisting of glycine ethyl ester; 2-(aminoethoxy)ethanol; 2,2'-(ethylenedioxy)bisethylamine; and 4,7,10-trioxa-1,3-tridecanediamine; wherein the particles covalently bind less than 0.35 milligrams per square meter of non-specific protein when contacted with serum; and wherein the particles physically adsorb less than 2 milligrams per square meter of non-specific protein when contacted with serum.

In yet another aspect of the invention, there is a reagent, comprising: a plurality of particles; each of said particles comprising a surface; an antibody bound to the surface through a covalent bond; and the reaction product of a succinimide ester and an amine compound of formula (I) on the surface;

H$_2$N—R—X  (I);

wherein —X is selected from the group consisting of —NH$_2$, —OH, and —CO$_2$CH$_2$CH$_3$; and R is selected from the group consisting of an alkyl group and an alkyl ether group; wherein, when —X is —NH$_2$ or —CO$_2$CH$_2$CH$_3$, R comprises from 1 to 20 carbon atoms; and when —X is —OH , R comprises from 4 to 20 carbon atoms.

In yet another aspect of the invention, there is an assay method for determining an antigen, comprising: combining a sample suspected of containing said antigen with the above reagent, the reagent comprising the antibody of said antigen, and the reagent capable of forming a detectable complex with said antigen; and determining the presence or amount of said detectable complex as a measure of said antigen in said sample.

In yet another aspect of the invention, there is a test kit, comprising the above reagent or any of the above particles.

DETAILED DESCRIPTION

Figure 1:
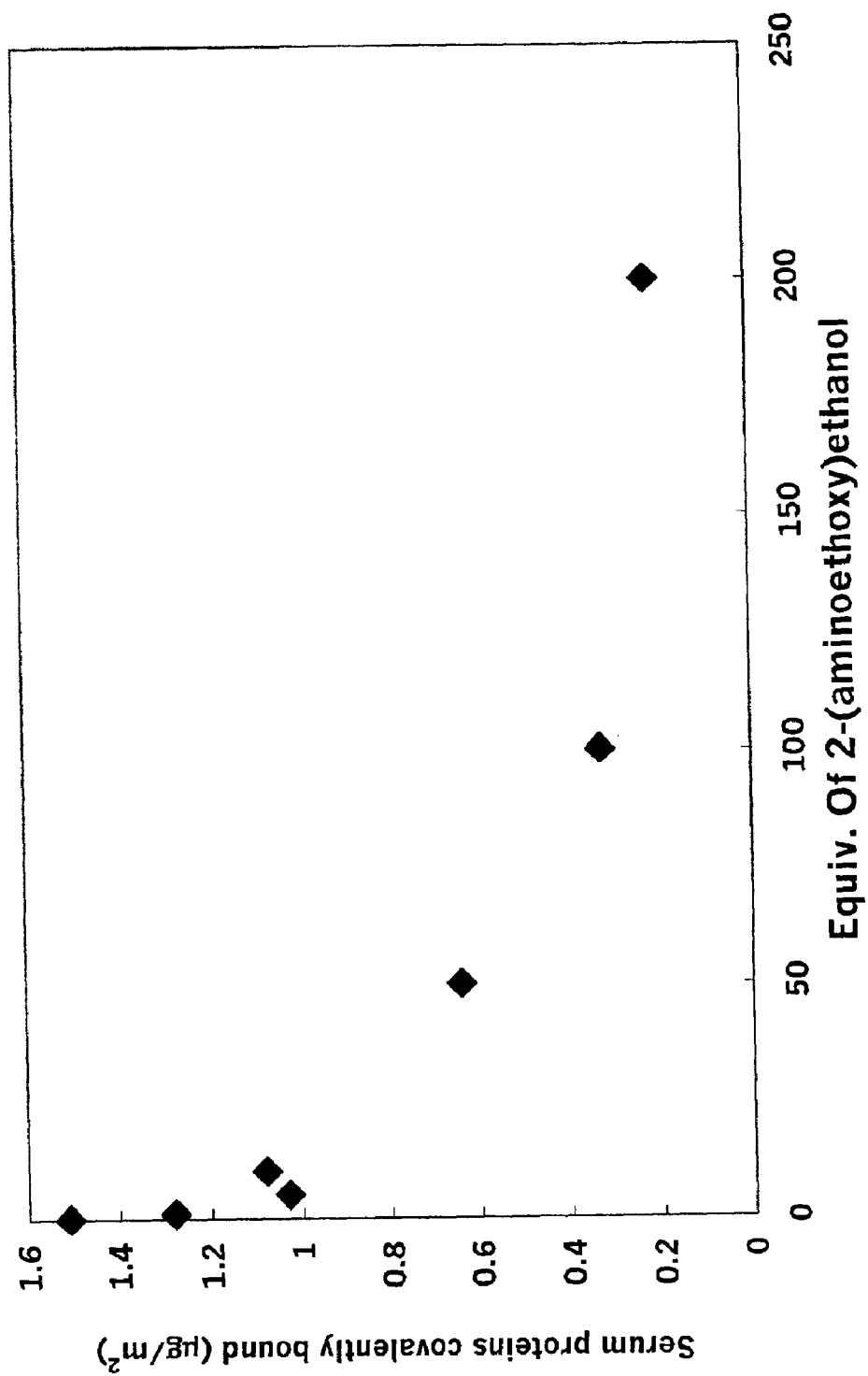
FIG. 1 is a graph of the dependence of covalent binding of serum proteins to carbodiimide-activated latex particles on the amount of 2-aminoethoxyethanol (AEO) added after EDC/NHS activation.

The present invention reduces interference in particle agglutination immunoassays. Particles which have been activated with N-hydroxysuccinimide or N-hydroxysulfosuccinimide and sensitized with an antibody are treated with certain amine compounds to reduce or eliminate residual N-hydroxysuccinimide (NHS) esters or N-hydroxysulfosuccinimide (sNHS) esters on the surface. Collectively, NHS-esters and sNHS-esters are referred to herein as "succinimide esters." The amine compounds used in the present invention are remarkably effective in the prevention of non-specific covalent interactions between sample components and reactive succinimide esters on the particles. Preferably, particles made by this method are also protected from physical adsorption of sample components. The present invention also relates to methods of making these particles and to their use in immunoassays.

The particles of the present invention contain an antibody on their surface, and the antibody undergoes a specific interaction with an analyte in the sample to be analyzed and with a conjugate of the analyte also present in the assay mixture. This interaction causes the particles to aggregate, and this aggregation can be monitored and correlated with the amount of the analyte in the sample.

Analyte refers to the substance, or group of substances, whose presence or amount thereof in a liquid medium is to be determined including, but not limited to, any drug or drug derivative, hormone, protein antigen, oligonucleotide, hapten, or hapten-carrier complex. An analyte analog is any substance, or group of substances, which behaves in a similar manner to the analyte, or in a manner conducive to achieving a desired assay result with respect to binding affinity and/or specificity of the antibody for the analyte including, but not limited to, derivatives, metabolites, and isomers thereof.

Antibody means a specific binding partner of the analyte and is meant to include any substance, or group of substances, which has a specific binding affinity for the analyte to the exclusion of other substances. The term includes polyclonal antibodies, monoclonal antibodies and antibody fragments.

Haptens are substances, typically of low molecular weight, which are not capable of stimulating antibody formation, but which do react with antibodies. The latter are formed by coupling the hapten to a high molecular weight carrier and injecting this coupled product into humans or animals. Examples of haptens include therapeutic drugs such as digoxin and theophylline; drugs of abuse such as morphine, lysergic acid diethylamide (LSD), and Δ9-tetrahydrocannabinol (THC); antibiotics such as aminoglycosides and vancomycin; hormones such as estrogen and progesterone; vitamins such as vitamin B12 and folic acid; thyroxin; histamine; serotonin; adrenaline and others.

A carrier refers to an immunogenic substance, commonly a protein, that can join with a hapten, thereby enabling the hapten to stimulate an immune response. Carrier substances include proteins, glycoproteins, complex polysaccharides and nucleic acids that are recognized as foreign and thereby elicit an immunologic response from the host.

The terms immunogen and immunogenic refer to substances capable of producing or generating an immune response in an organism.

A peptide is any compound formed by the linkage of two or more amino acids by amide (peptide) bonds, usually a polymer of α-amino acids in which the α-amino group of each amino acid residue (except the $NH_2$-terminal) is linked to the α-carboxy group of the next residue in a linear chain. The terms peptide, polypeptide and poly(amino acid) are used synonymously herein to refer to this class of compounds without restriction as to size. The largest members of this class are referred to as proteins.

A covalent bond is a chemical bond between two species, and may involve single bonds or multiple bonds. The term "covalent" does not include hydrophobic/hydrophilic interactions, Hydrogen-bonding, van der Waals interactions, and ionic interactions.

Any sample that is suspected of containing the analyte can be analyzed by the method of the present invention. The sample is typically an aqueous solution such as a body fluid from a host, for example, urine, whole blood, plasma, serum, saliva, semen, stool, sputum, cerebral spinal fluid, tears, mucus or the like, but preferably is urine, plasma or serum. The sample can be pretreated if desired and can be prepared in any convenient medium that does not interfere with the assay. An aqueous medium is preferred.

Calibration material means any standard or reference material containing a known amount of the analyte to be measured. The sample suspected of containing the analyte and the calibration material are assayed under similar conditions. Analyte concentration is then calculated by comparing the results obtained for the unknown specimen with results obtained for the standard.

Particles which may be treated according to the present invention include any type of particle which may be activated with succinimide esters. Such particles include polymer particles including polystyrene and poly(methylmethacrylate); gold particles including gold nanoparticles and gold colloids; and ceramic particles including silica, glass, and metal oxide particles. See for example C. R. Martin et al. *Analytical Chemistry—News & Features*, May 1, 1998, 322A–327A. These particles may be activated succinimide esters directly, or they may be activated once their surfaces have been modified to contain carboxylate groups. Carboxylate groups can be introduced to surfaces, for example by hydrolysis reactions, by treatment with a carboxylating reagent, or by formation of self-assembled monolayers (SAMs) containing carboxylate groups. See for example J. G. Chapman et al. *J. Am. Chem. Soc.*, 122, 8303–8304 (2000).

The particles of the present invention are particles which have been activated, sensitized, and then treated with an amine compound of formula (I):

$H_2N$—R—X (I);

where —X is —$NH_2$, —OH, or —$CO_2CH_2CH_3$; and R is an alkyl or alkyl ether group. When —X is —$NH_2$ or —$CO_2CH_2CH_3$, R contains from 1 to 20 carbon atoms. When —X is —OH, R contains from 4 to 20 carbon atoms. "Alkyl" refers to a substituted or unsubstituted, straight, branched or cyclic hydrocarbon chain. "Alkyl ether" refers to an alkyl group containing at least one —C—O—C— bond. Preferred amine compounds are those where —X is —OH or —$NH_2$, and R is an alkyl ether group containing from 4 to 20 carbon atoms and from 1 to 9 oxygen atoms. Particularly preferred amines are 2-(aminoethoxy)ethanol (AEO); 2,2'-(ethylenedioxy)bisethylamine (EBE); and 4,7,10-trioxa-1,3-tridecanediamine (TTD), which are represented by the following formulas:

$H_2N$—$CH_2CH_2OCH_2CH_2$—OH  (AEO);

$H_2N$—$(CH_2)_2O(CH_2)_2O(CH_2)_2$—$NH_2$  (EBE);

$H_2N$—$(CH_2)_3O(CH_2)_2O(CH_2)_2O(CH_2)_3$—$NH_2$  (TTD).

An illustration of the chemical reactions involved in the treatment process of the present invention is given in the following reaction scheme.

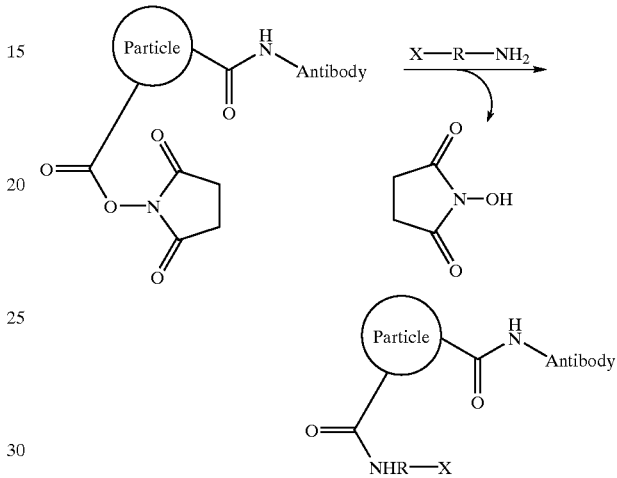

The nature and length of the —R— and —X moieties can significantly influence the effectiveness of an amine compound as a quenching reagent. For example, if —X is —$NH_2$ and R is of sufficient length, the reactive amine (—$NH_2$) groups at the termini of the compound can each interact with a succinimide ester group. This provides the compound with a "bidentate" character in which a single compound can react with two succinimide esters, provided the esters are sufficiently close to each other. Due to the proximal location of the first amine-succinimide ester reaction, the second reaction can proceed with a greater efficiency than the reaction of a free amine in solution. It is preferred that R contains at least 6 carbon atoms. More preferably, R contains at least 6 carbon atoms and at least 2 oxygen atoms. If R is too long, however, there is a risk of a single amine compound reacting with succinimide esters on different particles. This scenario would result in particles being linked together (crosslinked) with the R moiety as a bridge. The crosslinking of particles is generally undesirable since it is more difficult to distinguish between agglutinated and non-agglutinated samples. It is thus preferred that R contains 40 or fewer carbon atoms. More preferably, R contains 30 or fewer carbon atoms. Even more preferably, R contains 20 or fewer carbon atoms. The nature and length of the —R— moiety can also affect the tendency of sample components to physically adsorb onto the particle surface. The use of alkyl ether-based R moieties, particularly ethyleneoxy units (—$CH_2CH_2O$—), is believed to inhibit the physical adsorption of sample components on the particle surface (J. G. Chapman et al. *J. Am. Chem. Soc.*, 122, 8303–8304 (2000)).

The amine compounds are applied to the sensitized particles in an excess amount to provide for maximum reaction of the succinimide esters. Preferably, the particles are contacted with a solution containing at least 50 equivalents of the amine relative to the amount of carboxylate groups originally present on the particles before activation. More preferably, the particles are contacted with a solution containing at least 100 equivalents of the amine. Even more preferably, the particles are contacted with a solution containing at least 200 equivalents of the amine. The particles are exposed to the contacting solution for a time sufficient to allow an acceptable amount of reaction. This time may be from a few minutes to several hours. It is preferred that the contacting solution has a pH above 7.0. After the particles have been treated by exposure to the amine, the amine solution is washed from the surface of the particles. These particles thus have a surface which contains antibody, the reaction products of residual succinimide esters with the amine and, optionally, immobilized BSA.

These particles may be used in an immunoassay for the corresponding analyte of the antibody using standard immunoassay techniques.

Immunoassay mixtures using these particles may also contain a tertiary amine compound to reduce interference due to the presence of tertiary amine groups on the particle surface. Suitable tertiary amine compounds include triethanolamine (TEO), as described in co-pending application Ser. No. 10/025,378, entitled "Tertiary Amine Compounds For Use In Immunoassays" filed Dec. 18, 2001, with inventors C. C. Lawrence et al.

Particles of the present invention provide for a reduction in the amount of non-specific covalent binding of sample components. FIG. 1 illustrates the characteristics of particles which have been activated and treated with the amine, but which have not been reacted with antibody. Specifically, FIG. 1 is a graph of the amount of serum protein covalently bound to the particles as a function of the number of equivalents of the amine compound AEO added after the activation. Since no antibody is present, all proteins bound or adsorbed are non-specific proteins. Without amine treatment (zero equivalents of AEO), proteins from the serum mixture covalently bind to the activated particles, in this case providing a surface coverage of 1.5 milligrams per square meter ($mg/m^2$). Treatment with 200 equivalents of AEO, relative to the amount of carboxylate groups originally present, reduces the amount of covalently bound protein by about 85%.

The amount of non-specific protein covalently bound to particles is measured by the following test. A 750 microliter ($\mu$l) sample containing 0.5% (w/v) particles, 5% (v/v) normal human serum, and 50 mM 3-morpholino-propanesulfonic acid buffer (MOPS) at pH 7.0 is incubated at 37° C. for 2 hr and centrifuged (15,000×g, 30 min). The sample may not contain an antigen which will form a complex with any antibody bound to the particles. The particles are resuspended in 1 ml of 50 mM MOPS buffer at pH 7.0 and centrifuged again to remove excess, non-bound serum. This resuspension and centrifugation is repeated three more times. The resulting particles are resuspended by manual pipetting in 100 $\mu$l of a solution containing 6% (w/v) sodium dodecyl sulphate (SDS), 10% (v/v) glycerol and 60 mM Tris at pH 6.2, and are incubated at 80° C. for 2 hr to effect desorption of non-covalently bound species from the particle surface. The particles are collected by centrifugation (15,000×g, 1.5 hr), resuspended and washed three times with 1 ml volumes of 50 mM MOPS buffer at pH 7.0. The particles are finally resuspended in 100 $\mu$l of 50 mM MOPS buffer at pH 7.0, and are then subjected to an analysis of the protein content. The protein content analysis is the bicinchoninic acid (BCA) assay (PIERCE CHEMICAL COMPANY, Rockford, Ill.), performed according to the manufacturer's instructions. BCA assay samples are filtered through a 0.1 micrometer WHATMAN filter (FISHER SCIENTIFIC) prior to analysis at 562 nm. The protein content corresponds to the amount of protein which is covalently bound to the particles. This result can then be expressed as the mass of bound protein for a given overall surface area of the polymer particles used.

Preferably, the particles covalently bind less than 0.35 milligrams of non-specific protein per square meter of particle surface area in the above described test. More preferably, the particles covalently bind less than 0.30 milligrams per square meter ($mg/m^2$) of non-specific protein. Even more preferably, the particles covalently bind less than 0.20 $mg/m^2$ of non-specific protein. Even more preferably, the particles covalently bind less than 0.10 $mg/m^2$ of non-specific protein. Even more preferably, the particles covalently bind less than 0.05 $mg/m^2$ of non-specific protein.

Particles of the present invention also provide resistance to physical adsorption of sample components to the particle surface. The amount of non-specific protein physically adsorbed onto particles is measured by the following test. A 750 microliter ($\mu$l) sample containing 0.5% (w/v) particles, 5% (v/v) normal human serum, and 50 mM MOPS buffer at pH 7.0 is incubated at 37° C. for 2 hr and centrifuged (15,000×g, 30 min). The sample may not contain an antigen which will form a complex with any antibody bound to the particles. The particles are resuspended in 1 ml of 50 mM MOPS buffer at pH 7.0 and centrifuged again to remove excess, non-bound serum. This resuspension and centrifugation is repeated three more times. The resulting particles are resuspended by manual pipetting in 100 $\mu$l of a solution containing 6% (w/v) sodium dodecyl sulphate (SDS), 10% (v/v) glycerol and 60 mM Tris at pH 6.2, and are incubated at 80° C. for 2 hr to effect desorption of non-covalently bound species from the particle surface. The particles are collected by centrifugation (15,000×g, 1.5 hr), and the supernatant is subjected to an analysis of protein content by BCA assay. The protein content corresponds to the amount of protein physically adsorbed onto the particles. This result can then be expressed as the mass of adsorbed protein for a given overall surface area of the polymer particles used.

Preferably, the particles physically adsorb less than 3.0 milligrams of non-specific protein per square meter of particle surface area ($mg/m^2$) in the above described test. More preferably, the particles physically adsorb less than 2.0 $mg/m^2$ of non-specific protein. Even more preferably, the particles physically adsorb less than 1.0 $mg/m^2$ of non-specific protein.

Table 1 shows the amounts of serum proteins that were physically (non-covalently) adsorbed onto particle surfaces as a function of the number of equivalents of AEO used to quench the particles. These particles were not sensitized with an antibody but were activated and/or treated with AEO as indicated. In each case, the amount of passively adsorbed serum proteins is less than that using particles which had not been subjected to EDC activation (314 $\mu$g), and is comparable to that of particles which were activated but not treated with AEO (57 $\mu$g). Thus, not only does reaction of the residual succinimide esters on the particle surface with an amine of the present invention reduce the covalent binding of serum proteins to the particle during immunoassays, it also results in a surface which is resistant to physical adsorption of serum proteins. Both of these effects can enhance the performance of the immunoassay.

TABLE I

| Activated | AEO (equiv) | Serum proteins adsorbed | |
|---|---|---|---|
| | | μg | mg/m² |
| No | 0 | 314 | 3.14 |
| Yes | 0 | 57 | 0.57 |
| Yes | 1 | 66 | 0.66 |
| Yes | 5 | 55 | 0.55 |
| Yes | 10 | 73 | 0.73 |
| Yes | 50 | 78 | 0.78 |
| Yes | 100 | 72 | 0.72 |
| Yes | 200 | 116 | 1.16 |

Figure 3:
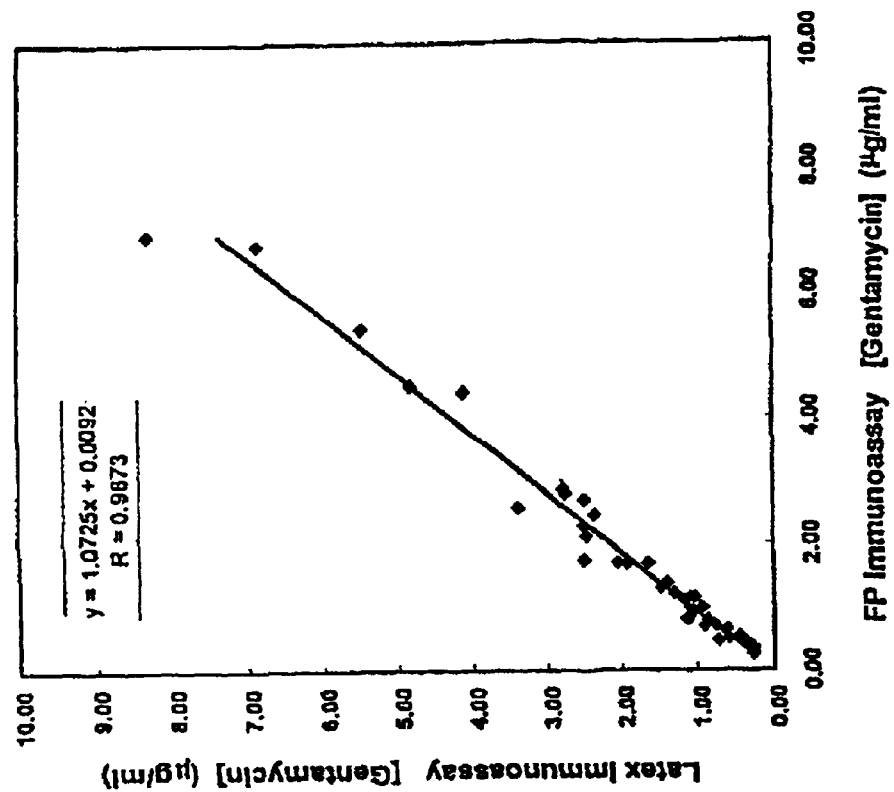
FIG. 3 is a graph correlating the measurements of gentamicin immunoassays performed by fluorescence polarization and by particle agglutination using particles which have been treated.
Figure 2:
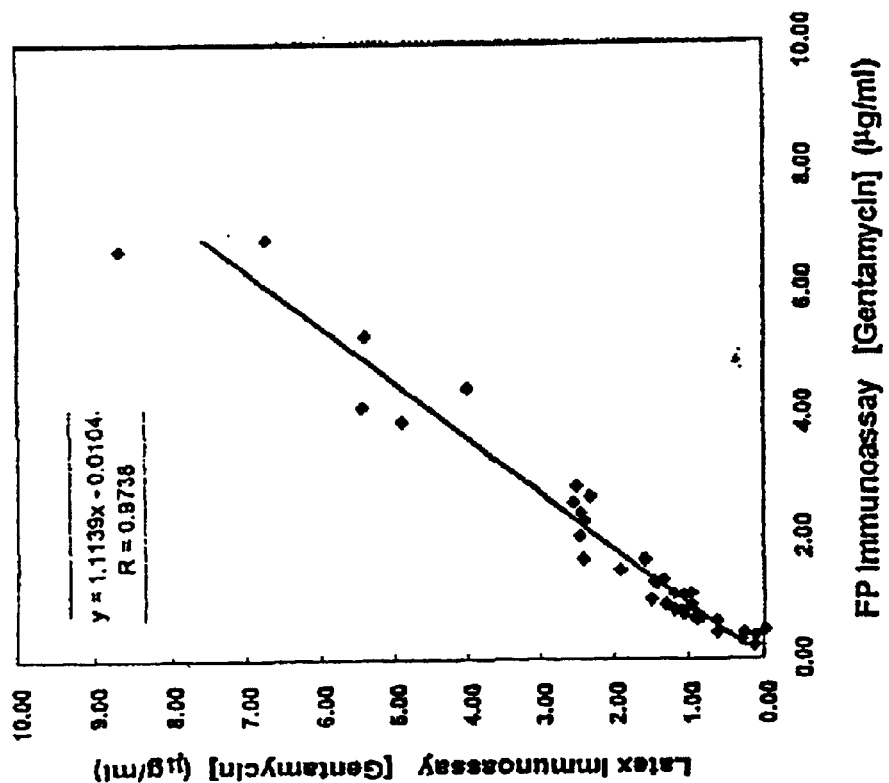
FIG. 2 is a graph correlating the measurements of gentamicin immunoassays performed by fluorescence polarization and by particle agglutination using untreated particles.

Although the particles of the present invention exhibit reduced interference in immunoassay conditions relative to conventional particles, they retain the ability to interact specifically with the antigen of interest. In fact, the performance of these particles as components of reagents for use in immunoassays is improved by the lack of interference. FIGS. 2 and 3 together illustrate the improved performance of particles of the present invention in an immunoassay. FIG. 2 is a graph correlating the measurements of an immunoassay for gentamicin performed by fluorescence polarization (FP) with the measurements of an immunoassay for gentamicin performed by particle agglutination using untreated particles. FIG. 3 is a graph correlating the same FP gentamicin measurements with gentamicin measurements from a particle agglutination immunoassay using particles which have been treated according to the present invention. The best-fit line correlating the data points should ideally be linear with a slope of 1, a y-axis intercept of zero, and a correlation coefficient (R) of 1. By each of these three measures the performance of the treated particles is superior to that of the untreated particles. The treated particles provide a slope of the best-fit line of 1.07, whereas the untreated particles provide a slope of the best-fit line of 1.11. The treated particles provide an intercept of 0.009, whereas the untreated provide an intercept of −0.010. The treated particles provide an R value of 0.987, whereas the untreated particles provide an R value of 0.974. Qualitatively, the correlation graph for the treated particles reproducibly exhibits less "scatter" than the correlation graph for the untreated particles.

When performing immunoassays of negative samples, which are assays of serum containing no analyte, particles of the present invention again provide for improved performance. Non-specific sample components, especially substances such as rheumatoid factor and cholesterol, can bind to conventional particles, causing an agglutination response similar to that caused by the specific reaction of an analyte with the particle. Thus, a sample may be improperly identified as containing the analyte. In negative samples which contain elevated contents of either rheumatoid factor or cholesterol, particles which have been treated with an amine compound according to the present invention provide for a lowering of the measured mean analyte concentration and standard deviation relative to particles which have not been subjected to an amine treatment step. That is, treated particles provide a measurement closer to the true value of zero, and the measurements are more consistent. The effect of including a treatment step in the particle preparation has an insignificant effect on the quality of the calibration curves obtained.

These results demonstrate that an improved performance of the particle based immunoassay can be obtained by treatment of the particles with an amine compound according to the present invention. During this step succinimide esters on the particle surface, formed during the carbodiimide-mediated activation reaction and not cleaved during sensitization with antibody and BSA, react with primary amine compounds. Failure to react the succinimide esters in this fashion can result in their reaction instead with serum components during the immunoassay. This in turn interferes with the kinetics and/or thermodynamics of the particle agglutination process, both in the case of serum samples which contain the target analyte and those samples which do not, leading in both cases to erroneous assay results.

The treatment of the particles with an amine compound of the present invention may be used alone or in combination with other techniques for reducing interference in an immunoassay. In optimizing the performance of particle agglutination immunoassays, it may be preferred to use sensitized particles which have been treated with a primary amine compound according to the present invention, and also to include a tertiary amine compound in the assay mixture as described in the above mentioned co-pending application Ser. No. 10/025,378, entitled "Tertiary Amine Compounds For Use In Immunoassays" filed Dec. 18, 2001, with inventors C. C. Lawrence et al. In some cases, the use of a tertiary amine compound such as TEO in the immunoassay mixture may be sufficient to reduce the interference of the immunoassay to the desired level. The use of either the primary amine particle treatment or the tertiary amine compound additive, alone or in combination, can be determined empirically to determine if one technique is better than the other or if the combination yields the best results.

Various ancillary materials will frequently be employed in an assay in accordance with the present invention. For example, buffers will normally be present in the assay medium, as well as stabilizers for the assay medium and the assay components. Frequently, in addition to these additives, additional proteins may be included, such as albumin; or surfactants may be included, particularly non-ionic surfactants and the like.

The particles may, along with other reagents, be packaged in a kit useful for conveniently performing the assay methods for the determination of an analyte. To enhance the versatility of the subject invention, reagents can be provided in packaged combination, in the same or separate containers, in liquid or lyophilized form so that the ratio of the reagents provides for substantial optimization of the method and assay. The reagents may each be in separate containers, or various reagents can be combined in one or more containers depending on the cross-reactivity and stability of the reagents.

For example, a reagent test kit which may contain, in packaged combination, an antibody specific for a particular analyte, a particle of the present invention containing the same antibody or an analog or derivative thereof, and may optionally also comprise one or more calibrators comprising a known amount of the analyte. Such a test kit may provide reagents for an assay with enhanced clinical sensitivity for the analyte and structurally related compounds.

EXAMPLES

The following examples are provided by way of illustration and should not be seen as limiting the scope of the present invention.

Latex particles having an average diameter of 201 nanometers (nm), a surface area of 28.4 square meters per gram ($m^2/g$), and containing 0.21 milliequivalents (meq) surface carboxylate groups per gram of latex were obtained from SERADYN (Indianapolis) and used without further characterization. Microparticle agglutination immunoassays were performed on a HITACHI 717 analyzer (ROCHE DIAGNOSTICS CORPORATION, Indianapolis) and their performance assessed with reference to results from ROCHE fluorescence polarization (FP) immunoassays which were conducted in parallel on an INTEGRA 700 analyzer (ROCHE DIAGNOSTICS SYSTEMS). ROCHE FP calibrators were used to construct a calibration curve for the microparticle-based assay. Protein content of solutions and latex particles was assessed by the bicinchoninic acid (BCA) assay (PIERCE CHEMICAL COMPANY, Rockford, Ill.) according to the manufacturer's instructions. BCA assay samples containing latex were filtered through a 0.1 μm WHATMAN filter (FISHER SCIENTIFIC) prior to analysis at 562 nm. Resuspension of latex pellets was effected using a ULTRASONIC HOMEGENIZER-4710 SERIES sonicator (COLE-PARMER, Vernon Hills, Ill.) at 25–50% output power while maintaining the sample on ice and latex monodispersity was assessed on a COBAS MIRA analyzer (ROCHE DIAGNOSTICS SYSTEMS) by light scattering at multiple wavelengths.

Solvents and buffers were obtained from FISHER SCIENTIFIC (Suwanee, Ga.). All other reagents were obtained from ALDRICH (Milwaukee, Wis.) or from FLUKA and were used as received.

Example 1

Effect of Treatment with Amine on Covalent Binding and Physical Adsorption of Serum Components to Activated Latex To a suspension of 1% (w/v) latex in 10 mM 2-morpholinoethane-sulfonic acid buffer (MES) having a pH of 5.0 and containing 21 millimolar (mM) N-hydroxysuccinimide (NHS), was added a fresh aqueous solution of 1-ethyl-3-(3-dimethylaminopropyl) carbodiimide (EDC), to a concentration of 21 mM. After incubation at room temperature for 2 hr, the suspension was spun down (15,000×g, 30 min) and the latex resuspended in 50 mM 3-morpholino-propanesulfonic acid buffer (MOPS) pH 8.0. To aliquots of this suspension was added 2-(aminoethoxy) ethanol (AEO) (in 50 mM MOPS buffer pH 8.0) to concentrations of 0 M, 0.002 M, 0.011 M, 0.021 M, 0.105 M, 0.210 M, and 0.420 M. The final volume of each of these suspensions was 1.1 ml containing 1% (w/v) latex. After incubation at room temperature for 2 hr, the latex was centrifuged (15,000×g, 30 min), resuspended in 1 ml of 50 mM MOPS buffer at pH 7.0, and centrifuged again. This process was repeated three more times. The final latex pellets were resuspended in 50 mM MOPS buffer at pH 7.0 and stored as 1% (w/v) suspensions at 4° C. for 48 hr.

Interaction of serum with these latex particles was examined as follows. Samples (750 microliters (μl)) containing 0.5% (w/v) latex particles as prepared above, 5% (v/v) normal human serum (SIGMA), and 50 mM MOPS buffer at pH 7.0 were incubated at 37° C. for 2 hr and centrifuged (15,000×g, 30 min). Separate control incubations in the absence of serum or using non-activated latex particles were also performed.

The pellets were resuspended in 1 ml of 50 mM MOPS buffer at pH 7.0 and centrifuged again to remove excess, non-bound serum. This process was repeated three more times. The resulting latex pellets were resuspended by manual pipetting in 100 μl of a solution containing 6% (w/v) sodium dodecyl sulphate (SDS), 10% (v/v) glycerol, and 60 mM Tris at pH 6.2, and were incubated at 80° C. for 2 hr to effect desorption of non-covalently bound species from the latex surface. The particles were collected by centrifugation (15,000×g, 1.5 hr) and the supernatants removed for determination of protein content by BCA analysis. The protein content corresponded to the amount of protein physically adsorbed onto the particles, and these results are given in Table 1.

The particles were resuspended and washed three times with 1 ml volumes of 50 mM MOPS buffer at pH 7.0. The particles were finally resuspended in 100 μl of 50 mM MOPS buffer at pH 7.0, and were then also subjected to BCA analysis of the protein content. The protein content corresponded to the amount of protein which had been covalently bound to the particles, and these results are given in FIG. 1.

Example 2

Effect of Treatment with Amine on Immunoassay Performance

To a 30 ml suspension of 1% (w/v) latex in 10 mM MES buffer at pH 5.0 was added 2.86 ml of a freshly prepared aqueous solution of 0.22 M NHS, followed by addition of 2.42 ml of a freshly prepared aqueous solution of 0.26 M EDC. The activation reaction was allowed to proceed for 2 hr at room temperature before collecting the latex by centrifugation (15,000×g, 45 min). The pellets were resuspended in 15 ml of 50 mM MOPS buffer at pH 6.4. To this suspension was added 15 ml of 50 mM MOPS buffer at pH 6.4 containing 50 mg/ml BSA and 0.30 mg/ml gentamicin monoclonal antibody M-12A9-IgG. The suspension was incubated at room temperature for 2 hr to effect sensitization. Excess IgG and BSA were removed by centrifugation (15,000×g, 30 min), and the pellets were resuspended in 15 ml of 50 mM MOPS buffer at pH 8.0. To this suspension was added 15 ml of 50 mM MOPS buffer at pH 8.0 containing 0.84 M AEO, followed by incubation at room temperature overnight to quench any NHS esters remaining on the latex surface after sensitization. Excess AEO was removed by repeated centrifugation and resuspension in 50 mM MOPS buffer at pH 8.0 (3 treatments of 30 ml each), and the resulting latex stored as a 2% (w/v) suspension in 50 mM MOPS buffer at pH 7.5, containing 0.1% (w/v) BSA and 0.1% (w/v) $NaN_3$. A control batch of latex was made in parallel in an identical fashion except that the AEO quenching step was omitted. The performance of the quenched and control particles were assessed by immunoassay against a series of clinical serum samples.

The gentamicin content of each sample was determined by the ROCHE FP gentamicin immunoassay using the same gentamicin monoclonal antibody as the latex-based assay. The FP reference immunoassays and the latex agglutination immunoassays were performed in parallel to avoid sample degradation. The correlation of the gentamicin concentration as measured by the ROCHE FP system with the gentamicin concentrations as measured by the particle-based agglutination assays are shown in FIGS. 2 and 3.

Example 3

Immunoassays of Negative Samples

Immunoassays were also run on a set of thirty serum samples which tested negative for gentamicin by the Roche FP immunoassay. The mean apparent gentamicin concentration for this sample set was −0.03 μg/ml with a standard deviation of 0.17 μg/ml for the quenched latex, compared to values of −0.09 µg/ml and 0.31 µg/ml respectively for the unquenched latex.

Example 4

Additional Amine Compounds for Efficient Treatment

To a suspension of 50 ml of 1% (w/v) latex in 10 MES buffer at pH 5.0, was added 4.78 ml of a freshly prepared aqueous solution of 0.22 M NHS, followed by 4.03 ml of a freshly prepared aqueous solution of 0.26 M EDC. After incubation at room temperature for 2 hr the suspension was centrifuged (15,000×g, 30 min) and the latex resuspended in 50 mM MOPS buffer at pH 8.0 to give a 2% (w/v) suspension. The suspension was divided into 1.5 ml aliquots, and to each one was added 1.29 ml of a 1 M solution of one of the following amine compounds: hydroxylamine; ethanolamine; 2-(methylamino)ethanol; diethanolamine; glycine; glycine ethyl ester; sarcosine; sarcosine ethyl ester; (methylamino)acetaldehyde dimethyl acetal; N-methyl-D-glucamine; AEO; EBE; and TTD. Each compound was added as a solution of its hydrochloride salt in 50 mM MOPS buffer at pH 8.0. Separate control experiments were performed in the absence of any amine or using latex which was not subjected to the activation reaction. The reaction mixtures were incubated at room temperature for 2 hr and then centrifuged (15,000×g, 30 min). Excess amine was removed by washing the latex with 3 treatments of 1 ml of 50 mM MOPS buffer at pH 7.0. The final latex pellets were resuspended in 50 mM MOPS buffer at pH 7.0 and stored as 2% (w/v) suspensions at 4° C. for 48 hr.

Interaction of serum with these latex particles was examined. Samples (750 µl) containing 0.5% (w/v) latex particles prepared above, 5% (v/v) normal human serum, 50 mM MOPS buffer at pH 7.0 were incubated at 37° C. for 2 hr and then centrifuged (15,000×g, 30 min). A control incubation in the absence of serum was performed for selected latices. The pellets were resuspended in 1 ml of 50 mM MOPS buffer at pH 7.0 and centrifuged again to remove excess, non-bound serum. This process was repeated three more times. The resulting latex pellets were resuspended by manual pipetting into 100 µl of a solution containing 6% (w/v) SDS, 10% (v/v) glycerol, and 60 mM Tris pH 6.2, and then incubated at 80° C. for 2 hr to effect desorption of non-covalently bound species from the latex surface. The particles were collected by centrifugation (15,000×g, 1.5 hr) and the supernatants removed for BCA analysis. The particles were resuspended and washed with 3 treatments of 1 ml of 50 mM MOPS buffer at pH 7.0. The particles were finally resuspended in 100 µl of 50 mM MOPS buffer at pH 7.0 and subjected to BCA analysis to evaluate the quenching of each of the tested compounds.

Table 2 shows the quantity of proteins in the serum samples which became covalently bound to each of the activated-treated latices, as determined by the BCA assay.

TABLE 2

| Activated | Amine Compound | Molecular Formula | Serum proteins bound, (mg/m$^2$) |
|---|---|---|---|
| No | None | | 0.13 |
| Yes | None | | 0.89 |
| Yes | Sarcosine ethyl ester | MeNHCH$_2$CO$_2$Et | 1.31 |
| Yes | Sarcosine | MeNHCH$_2$CO$_2$H | 1.25 |
| Yes | Diethanolamine | HN(CH$_2$CH$_2$OH)$_2$ | 0.98 |
| Yes | Glycine | H$_2$NCH$_2$CO$_2$H | 0.95 |
| Yes | N-Methyl-D-glucamine | MeNHCH$_2$(CHOH)$_4$CH$_2$OH | 0.94 |
| Yes | 2-(Methylamino)ethanol | MeNHCH$_2$CH$_2$OH | 0.91 |
| Yes | (Methylamino)-acetaldehyde dimethyl acetal | MeNCH$_2$CH(OCH$_3$)$_2$ | 0.85 |
| Yes | Hydroxylamine | NH$_2$OH | 0.70 |
| Yes | Ethanolamine | H$_2$NCH$_2$CH$_2$OH | 0.42 |
| Yes | Glycine ethyl ester | H$_2$NCH$_2$CO$_2$CH$_2$CH$_3$ | 0.29 |
| Yes | 2-(Aminoethoxy)ethanol (AEO) | H$_2$NCH$_2$CH$_2$OCH$_2$CH$_2$OH | 0.28 |
| Yes | 2,2'(ethylenedioxy)-bisethyl-amine (EBE) | H$_2$N(CH$_2$)$_2$O(CH$_2$)$_2$O(CH$_2$)$_2$NH$_2$ | 0.00 |
| Yes | 4,7,10-Trioxa-1,3-tridecanediamine (TTD) | H$_2$N(CH$_2$)$_3$O(CH$_2$)$_2$O(CH$_2$)$_2$O-(CH$_2$)$_3$NH$_2$ | 0.05 |

The data reveals that of the thirteen compounds tested, only five efficiently react with the succinimide ester functionalities on the surface of the latex under these conditions: ethanolamine, glycine ethyl ester, AEO, EBE and TTD. All of these allow less than 0.50 mg/m$^2$ of protein to covalently bind to the particles. Of these efficient amine compounds, AEO and the two diamino compounds EBE and TTD allow less than 0.30 mg/m$^2$ of protein to covalently bind to the particles, a significant improvement over the conventional amines ethanolamine (0.42 mg/m$^2$) and glycine (0.95 mg/m$^2$).

The two compounds EBE and TTD and their analogs are potentially interesting treatment molecules because of a single molecule's ability to cleave two succinimide esters, thereby forming a closed surface element on a latex particle which would be expected to be especially resistant to interactions with serum components. A monodispersity check of the EBE- and TTD-treated latices revealed that cross-linking of the diamines between latex particles had not occurred.

Upon analysis of the desorption supernatants in this serum adsorption experiment, the amounts of serum proteins passively adsorbed to these latices relative to the control latex which had not been activated, were 39% (AEO), 41% (EBE) and 36% (TTD). Thus upon reaction of remaining succinimide ester groups on the latex by AEO, EBE and TTD, latex surfaces are created which have the desirable property of being moderately resistant to physical adsorption of serum proteins. These latices, by virtue of having minimal interactions with serum proteins either by irreversible (covalent) binding or by reversible (passive) binding, are suitable for immunoassay development.

Example 5

Use of Triethanolamine as an Additive to Improve Immunoassay Performance

Latex agglutination immunoassays were performed using latex particles which had been sensitized with a gentamicin monoclonal antibody and treated with AEO. Immunoassays were performed in the absence of triethanolamine (TEO) and in the presence of TEO at final concentrations in the range of 2.5–15 mM. The gentamicin content of each serum sample tested was determined by the commercially available Roche FP gentamicin immunoassay which uses the same gentamicin monoclonal antibody as the latex-based assay. The FP reference immunoassays and the latex agglutination immunoassays were performed in parallel to avoid sample degradation. The inclusion of TEO in the latex immunoassay buffer did not significantly affect the quality of the calibration curve obtained.

Figure 5:
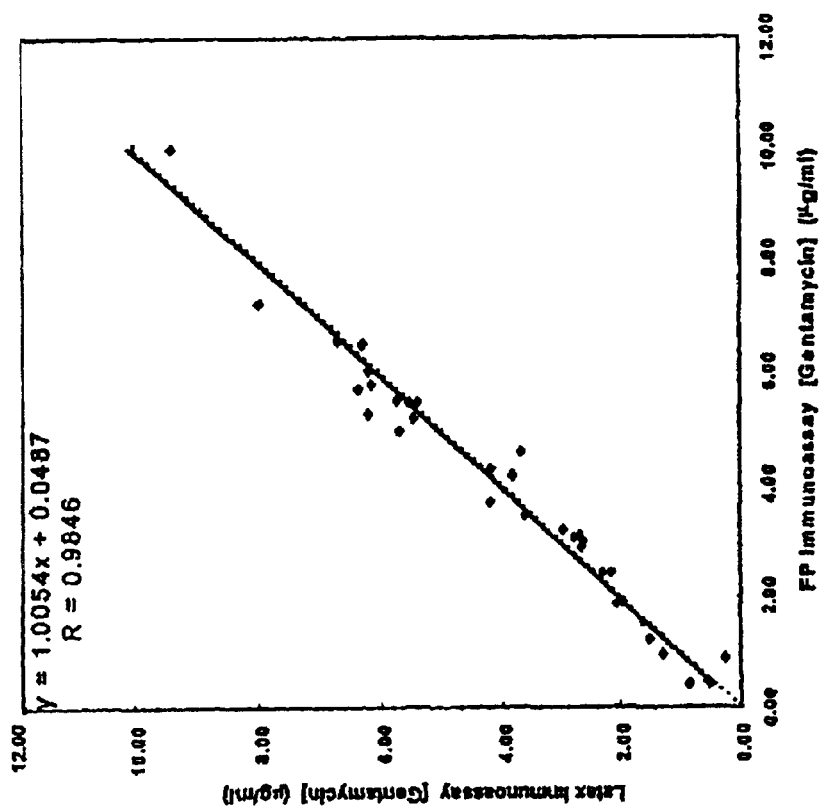
FIG. 5 is a graph correlating the measurements of gentamicin immunoassays performed by fluorescence polarization and by particle agglutination with TEO present.
Figure 4:
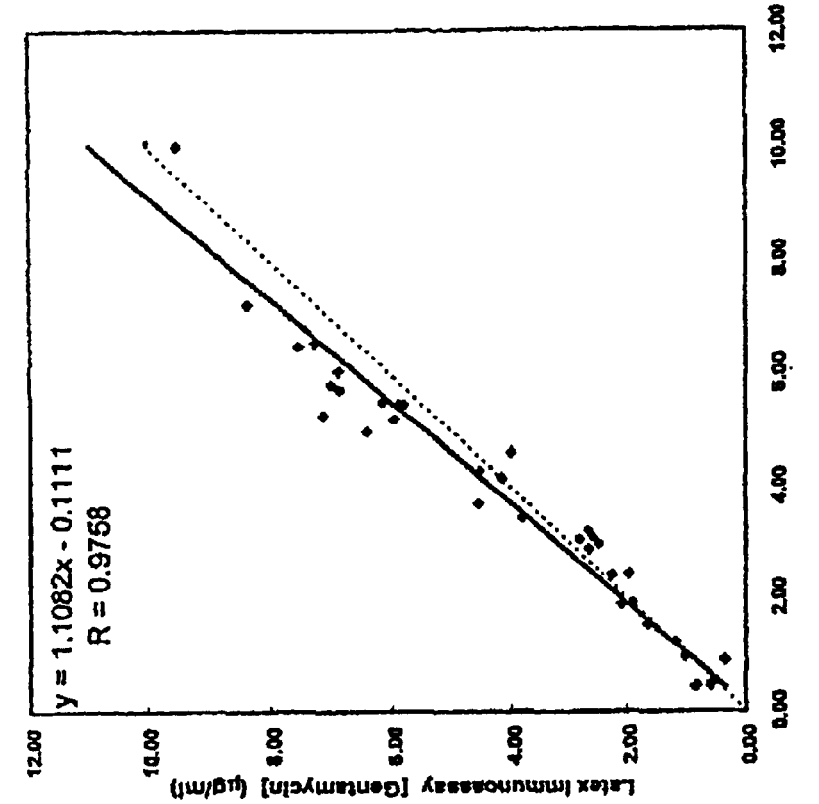
FIG. 4 is a graph correlating the measurements of gentamicin immunoassays performed by fluorescence polarization and by particle agglutination without triethanolamine (TEO) present.

FIGS. 4 and 5 show correlation graphs of the microparticle-based immunoassays either in the absence of TEO or in the presence of 12.5 mM TEO, with the Roche FP immunoassay. Inclusion of TEO as an additive has a dramatic effect on the performance of the latex agglutination immunoassay. Relative to the control experiment (no TEO), the slope of the best-fit line decreases from 1.11 to 1.01, the y-axis intercept changes from −0.11 to 0.05 and the R correlation coefficient increases from 0.976 to 0.985. Thus the three parameters move closer to the optimal values of 1.00, 0.00 and 1.000 respectively, as is visually apparent from the merging of the best-fit line (solid line) to the target line (dotted line (slope=1, intercept=0)). A similar beneficial effect of including TEO in the microparticle based assay formulation was seen when the latex was tested with a set of serum samples which had tested negative for gentamicin by the Roche FP immunoassay. When the final assay mixture contained 12.5 mM TEO, the mean apparent gentamicin concentration in this sample set was −0.32 μg/ml compared to 0.42 μg/ml in the absence of TEO. The desired lower limit of detection of this assay is 0.17 μg/ml. Optimization studies suggested that a final TEO concentration of 5 mM was sufficient for the benefits afforded by this additive to be fully realized.

What is claimed is:

1. A method of preparing particles for immunoassays, comprising:
  reacting particles comprising carboxylate groups with N-hydroxysuccinimide or N-hydroxysulfosuccinimide and with a carbodiimide coupling reagent to provide activated particles comprising succinimide ester groups;
  contacting said activated particles with antibodies to provide sensitized particles comprising covalently bound antibodies and residual succinimide esters; and
  treating said sensitized particles in an aqueous mixture with an amine compound selected from the group consisting of 2,2'-(ethylenedioxy)bisethylamine and 4,7,10-trioxa-1,3-tridecanediamine
  wherein the treatment results in the reaction of the succinimide ester groups with the amine functionality of the amine compound to form an amide linkage.

2. The method of claim 1, wherein the ratio of equivalents of amine compound to equivalents of carboxylate groups is at least 50.

3. The method of claim 1, wherein the aqueous mixture has a pH of at least 7.0.

4. The method of claim 1, wherein the particles covalently bind less than 0.35 milligrams per square meter of non-specific protein when contacted with serum.

5. The method of claim 1, wherein the particles physically adsorb less than 3 milligrams per square meter of non-specific protein when contacted with serum.

6. A sensitized particle for use in immunoassays, comprising:
  a particle comprising a surface;
  at least one antibody bound to the surface through a covalent bond from reaction of an N-hydroxysuccinimide or N-hydroxysulfosuccinimide/carbodiimide-activated carboxylate group on the particle surface with an amine group on the antibody; and
  the reaction product of a succinimide ester on the surface and an amine compound selected from the group consisting of 2,2'-(ethylenedioxy)bisethylamine and 4,7,10-trioxa-1,3-tridecanediamine,
  the reaction product being covalently attached to the particle surface.

7. The sensitized particle of claim 6, further comprising BSA on the surface.

8. The sensitized particle of claim 6, wherein the particle comprising a surface is selected from the group consisting of gold particles, ceramic particles, and polymer particles.

9. The sensitized particle of claim 6, wherein the particles covalently bind less than 0.35 milligrams per square meter of non-specific protein when contacted with serum.

10. The sensitized particle of claim 6, wherein the particles physically adsorb less than 3 milligrams per square meter of non-specific protein when contacted with serum.

11. A particle for use in immunoassays, comprising:
  a polymer particle comprising a surface;
  at least one antibody bound to the surface through a covalent bond from reaction of an N-hydroxysuccinimide or N-hydroxysulfosuccinimide/carbodiimide-activated carboxylate group on the particle surface with an amine group on the antibody;
  BSA on the surface; and
  the reaction product of a succinimide ester and an amine compound on the surface;
    wherein the amine compound is selected from the group consisting of 2,2'-(ethylenedioxy)bisethylamine and 4,7,10-trioxa-1,3-tridecanediamine;
    wherein the reaction product is covalently attached to the particle surface;
    wherein the particles covalently bind less than 0.35 milligrams per square meter of non-specific protein when contacted with serum; and
    wherein the particles physically adsorb less than 2 milligrams per square meter of non-specific protein when contacted with serum.

12. A reagent, comprising:
  a plurality of particles;
  each of said particles comprising a surface;

an antibody bound to the surface through a covalent bond from reaction of an N-hydroxysuccinimide or N-hydroxysulfosuccinimide/carbodiimide-activated carboxylate group on the particle surface with an amine group on the antibody; and the reaction product of a succinimide ester on the surface and an amine compound selected from the group consisting of 2,2'-(ethylenedioxy)bisethylamine and 4,7,10-trioxa-1,3-tridecanediamine, the reaction product being covalently attached to the particle surface.

13. An assay method for determining an antigen, comprising:

combining a sample suspected of containing said antigen with the reagent of claim 12, the reagent comprising the antibody of said antigen, and the reagent capable of forming a detectable complex with said antigen; and determining the presence or amount of said detectable complex as a measure of said antigen in said sample.

14. A test kit, comprising the reagent of claim 12.

* * * * *